United States Patent
Putnam et al.

(10) Patent No.: US 8,968,681 B2
(45) Date of Patent: Mar. 3, 2015

(54) FILTERED ASSAY DEVICE AND METHOD

(75) Inventors: David L. Putnam, Sammamish, WA (US); Jason A. Putnam, Sammamish, WA (US); Todd W. Hubbard, Seattle, WA (US)

(73) Assignee: Photonic Biosystems Inc., Sammamish, WA (US)

( * ) Notice: Subject to any disclaimer, the term of this patent is extended or adjusted under 35 U.S.C. 154(b) by 496 days.

(21) Appl. No.: 12/582,425

(22) Filed: Oct. 20, 2009

(65) Prior Publication Data

US 2010/0133175 A1  Jun. 3, 2010

Related U.S. Application Data

(60) Provisional application No. 61/106,622, filed on Oct. 20, 2008.

(51) Int. Cl.
*G01N 1/40* (2006.01)
*C12Q 1/24* (2006.01)

(52) U.S. Cl.
CPC ......... *C12Q 1/24* (2013.01); *G01N 1/405* (2013.01); *G01N 2001/4088* (2013.01)
USPC .................... 422/534; 435/308.1; 210/436

(58) Field of Classification Search
CPC ... C12Q 1/24; G01N 1/405; G01N 2001/4088
See application file for complete search history.

(56) References Cited

U.S. PATENT DOCUMENTS

| | | | |
|---|---|---|---|
| 2,904,474 A | 9/1959 | Förg | 195/139 |
| 3,928,139 A | 12/1975 | Dorn | 195/103.5 R |
| 4,336,337 A | 6/1982 | Wallis et al. | 435/292 |
| 4,411,783 A * | 10/1983 | Dickens et al. | 210/304 |
| 4,867,885 A | 9/1989 | Yen | |
| 5,055,198 A | 10/1991 | Shettigar | |
| 5,081,017 A | 1/1992 | Longoria | 435/30 |
| 5,092,996 A * | 3/1992 | Spielberg | 210/232 |
| 5,342,519 A * | 8/1994 | Friedmann et al. | 210/232 |
| 5,420,017 A | 5/1995 | Tuompo et al. | 435/29 |

(Continued)

OTHER PUBLICATIONS

"Autoclave Temperature and Time Pressure Chart" Website accessed by the examienr at <http://www.sterilizers.com/autoclave-time-temperature-pressure-chart.html> on Sep. 12, 2011.*

(Continued)

*Primary Examiner* — Christopher A Hixson
(74) *Attorney, Agent, or Firm* — Morgan Lewis & Bockius LLP (57) ABSTRACT

A method and device is provided for collecting filterable material to perform assays on a filtration apparatus by applying negative-pressure to the inlet chamber of the filtration apparatus which is independent of negative or positive pressure applied to its fluid path. The negative-pressure applied to the inlet chamber serves to actively aspirate fluid and promote flow into the inlet chamber via the fluid pathway. The negative-pressure applied to the inlet chamber facilitates the use of either negative or positive-pressure based fluid-filtration approaches. Use of the invention improves the functionality and scope of applications that can be performed with enclosed filtration apparatuses.

19 Claims, 7 Drawing Sheets

(56) References Cited

U.S. PATENT DOCUMENTS

| | | | | |
|---|---|---|---|---|
| 5,423,759 A | * | 6/1995 | Campbell | 604/153 |
| 5,861,270 A | | 1/1999 | Nelis | 435/34 |
| 6,302,860 B1 | * | 10/2001 | Gremel et al. | 604/6.09 |
| 6,670,145 B2 | | 12/2003 | Brenner et al. | 435/29 |
| 2003/0082516 A1 | | 5/2003 | Straus | 435/4 |
| 2004/0188344 A1 | * | 9/2004 | Scott et al. | 210/406 |
| 2007/0003997 A1 | | 1/2007 | Kemmochi et al. | 435/34 |
| 2007/0281291 A1 | | 12/2007 | Kuchta | 435/4 |

OTHER PUBLICATIONS de Vries, Adrianus J. et al. "Clinical evaluation of a new fat removal filter during cardiac surgery." European Journal of Cardiothoracic Surgery (2004) 25 261-266.*

International Search Report and Written Opinion for PCT/US2009/005704, date of mailing July 1, 2010.

* cited by examiner

Figure 1 of 7. Isometric View

Figure 2 of 7. Exploded Detail A

Vent Region

Figure 3 of 7. Side View

Figure 4 of 7. Exploded Detail B

Vent & Port (Side View)

Figure 5 of 7. Isometric View

Figure 6 of 7. Detail C Section View

Figure 7 of 7.

FILTERED ASSAY DEVICE AND METHOD

CROSS-REFERENCE TO RELATED APPLICATIONS

This application claims the benefit of U.S. Provisional Application No. 61/106,622, which was filed on Oct. 20, 2008, hereby incorporated by reference.

STATEMENT REGARDING FEDERALLY SPONSORED RESEARCH

The U.S. Government owns rights in the present invention pursuant to contract number W81XWH-04-C-0149 from the United States Department of Defense through the US Army Medical Research Acquisition Activity.

BACKGROUND OF THE INVENTION

Fluid filters consisting of a filtering element interposed in a fluid path exist in many forms. The fluid path typically has a reservoir or chamber to receive fluid on the inlet side of a filter element and a housing to hold and support the filter element. On the outlet or discharge side of the filter element the fluid path commonly includes another chamber with an outlet port to receive the clean filtered fluid and convey the fluid away. The filtration process requires either applying positive-pressure from a pump or a gravity-feed on a fluid stream to push it through the inlet chamber and the filter element, or negative-pressure applied at the outlet side to pull fluid through the filter element.

Filters are commonly used to remove particulate matter from fluid streams in order to prepare clarified fluid. The filter element is typically enclosed in a cartridge or housing to protect it and the fluid content from external exposure and contaminates. Enclosed or encapsulated cartridge-type filters of this type with inlet and outlet chambers and respective inlet and outlet ports for the fluid path are often referred to as in-line fluid filters.

There are common problems associated with fluid filtration using enclosed filter cartridges or capsules, especially those having small internal volume, e.g., <5 mL. For example, to process aqueous solutions the typical filter elements are hydrophilic porous membranes. Such membranes once wetted do not typically pass air under normal conditions of use. Difficulties are encountered if air enters the inlet chamber of an enclosed filtration apparatus after the initial introduction of fluid. Trapped air will impede and can completely prevent flow. Air in contact with the filter membrane occludes fluid flow. An accumulation of air covering the filter element creates an "air-lock" that completely blocks fluid flow, regardless of whether the filtration is based on a negative or positive-pressure fluid flow approach. Vacuum at the outlet side cannot pull the blocking air through the filter element to allow fluid to enter the inlet chamber, which is needed to resume flow. Nor can fluid necessarily be pushed by positive pressure into an air-locked inlet chamber because of the air blocking the fluid path.

Several approaches have been designed to alleviate the problem of air blockage and locking in filtration devices with enclosed inlet chambers. One is to incorporate a passive vent into the inlet chamber so that there is an air release or escape path. For aqueous filtration, such devices may cover the vent hole with a porous hydrophobic membrane, e.g., PTFE, which prevents fluid passage and leakage from the device, but allows air to exit via the vent.

The inlet-chamber passive vent generally only works, however, if the filtration system is based on fluid positive pressure and not a negative-pressure approach. It requires that fluid be pushed in via the inlet port and relies on that flow to dispel the air from the inlet chamber such that fluid contacts the filter element and hence passes through it. In contrast, regardless of venting of the inlet chamber, vacuum applied to the outlet side of a wetted membrane is ineffectual for ridding an air-locked inlet chamber of air and allowing fluid flow. A vacuum at the outlet will not pull air through the wetted membrane and will not create a negative pressure in the inlet chamber. Moreover, it is impractical because the passive vent on the inlet chamber constitutes a pathway for air to leak into or be pulled into the inlet chamber as fluid is drawn through, thus promoting air-lock conditions.

Another approach for voiding air from an inlet chamber and circumventing air locks has been the design of special vented filter elements. These incorporate regions that are hydrophilic for fluid filtration, and also have hydrophobic regions specifically for venting air through the filter. These devices avoid problems of complete locking and can be used with either positive or negative-pressure based filtration system. However, their shortcomings are that air passage through the membrane may be undesirable, inclusion of the venting regions reduces fluid flow efficiency and may be only partially effective at voiding trapped air, and the special membrane is higher cost.

In summary, problems are encountered with current devices and practices that impact filter performance and impede or completely block fluid flow in filtration devices with enclosed inlet chambers. There are partial solutions using vented cartridges and other deficiencies with vented-filters, which are the alternative for negative-pressure systems.

The present invention overcomes these insufficiencies in a practical manner enabling enclosed filtration devices to be used with both positive pressure, and more attractively, negative-pressure filtration systems in applications that heretofore were untenable. It does so by providing simple and practical means for actively applying negative-pressure to the inlet chamber to aspirate air and/or fluid while either negative or positive pressure is independently employed to move fluid through the filter element.

SUMMARY OF THE INVENTION

The present invention provides for a method and device to apply negative-pressure to the inlet chamber of a filtration apparatus in order to actively evacuate the inlet chamber and fill it with fluid. Its application is independent of either a positive-pressure or negative pressure being otherwise applied to the fluid path of the filter apparatus. The purpose of the actively applied negative pressure is to enable aspiration of fluid or air, facilitate the flow of fluid into the inlet chamber, remove air from the inlet chamber, ensure the filter element is optimally in contact with fluid and not air, and enable the filtration apparatus to operate most efficiently.

The inventive method and device further provides for the inclusion of use of either negative or positive-pressure based systems to effect fluid flow through the fluid path of the filtration apparatus. Various combinations of approaches to create negative pressure in the inlet chamber and effect fluid flow become practical. One of the most advantageous embodiments includes the application of a vacuum to a breathable vent on the inlet chamber in order to pull air out and fluid into the inlet chamber, and the application of vacuum at an outlet port to pull filtered fluid through the filter membrane. The latter, by itself, had limited practical application prior to the inventive method.

The inventive method and device provides for the inclusion of controlling means so that the delivery of actively applied negative pressure at the inlet chamber vent, and the fluid flow system (either negative or positive-pressure based), can be regulated and actuated independently in order to achieve application specific objectives with the filter apparatus. The inventive method and device use to specific advantage the property of wetted hydrophilic filter membranes not passing air and the fact that an air-locked filter will neither allow fluid or air to pass through it.

Procedures are identified for use of the method and device to inventively harvest and concentrate filterable matter in an enclosed filter apparatus and prepare the collected sample for analysis. The filter apparatus is employed as a self-contained, multifunctional, assay-system providing for rinsing of the captured matter, exposure to reagents, culture of cells in a protected environment, and analytical testing.

Inclusive with the invention is a method and device for controlling, on the outlet side of the filter element, the volume of fluid that is filtered through a filtration apparatus. It consists of an enclosed fluid reservoir with means to manage, define, and limit the volume of filtered fluid.

DESCRIPTION OF THE DRAWINGS

FIG. 2 shows schematically the vent (202) on the inlet-chamber and the fluid outlet port (201) that communicates with the outlet chamber on the opposing side.

FIG. 4 shows schematically the vent hole (404) on the inlet-chamber (402) with a porous hydrophobic membrane (405) covering the hole that allows passage of air, but not fluid, and protects the contents of the device. The porous hydrophilic membrane (406) situated between the inlet and outlet chambers is identified. Also pictured are the fluid outlet port (401) and the outlet chamber (403).

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

This invention applies to the use of filter apparatuses of the "in-line" filter type having a filter element enclosed in a cartridge or capsule, or at least associated with an enclosed inlet chamber. Objectives of the invention are to: promote filling of the inlet chamber with fluid (in particular with wetted filter elements), to void air, to prevent air-locks, and to maintain fluid flow so that fluid filtration in the apparatus is conducted in a most efficient manner. It accomplishes this and provides for other enablements by applying negative-pressure to the inlet chamber. The independent application of negative pressure to the inlet chamber is itself of importance, irrespective of either positive or negative-pressure on the fluid stream being used to push or pull fluid through the filter apparatus.

For example, in-line filters are used in medical practice to deliver intravenous solutions. The filters serve two purposes: to ensure that the fluid delivered is sterile filtered; and to remove air from the fluid path. Pumped or gravity-fed fluid under positive-pressure is delivered to the IV filter which has a vented inlet chamber. The vent is covered with a breathable microporous hydrophobic membrane to prevent both fluid exit and entry of microbial contaminates. Air in the incoming fluid stream entering the inlet chamber is able to escape through the vent. Egress is contingent upon the rate and pressure head produced by the incoming fluid stream, which is required to push and dispel air out the vent. The efficiency of air evacuation, and filter performance (e.g., filter membrane surface area not occluded by air and available to filtration) depends upon several variables: filter and vent size and configuration, filter orientation and location of the vent relative to the inlet port, and delivered-fluid pressure.

Figure 1:
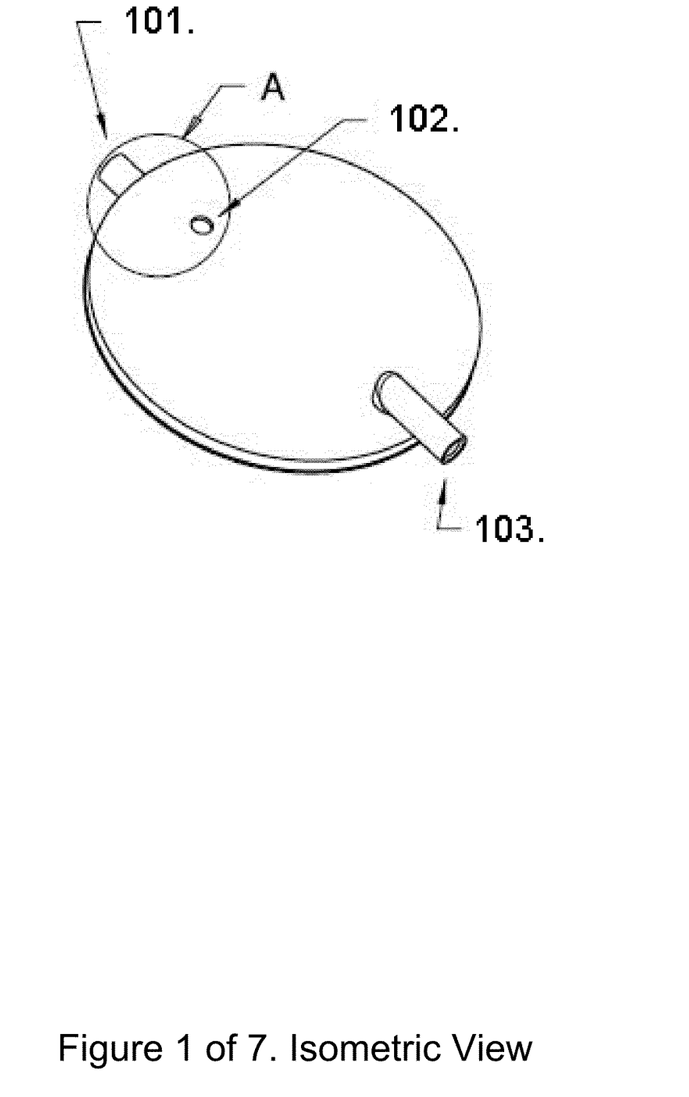
FIG. 1 is an isometric view illustrating an exemplary vented cartridge filter (VCF) in a round planar enclosure holding internally a circular porous filter membrane. The fluid inlet port (103) is identified whereby fluid is introduced to the inlet-chamber side of the device. The vent (102) incorporated into the inlet chamber for air egress is indicated. The fluid outlet port (101) shown is on the opposing or outlet-chamber side of the enclosure.
Figure 2:
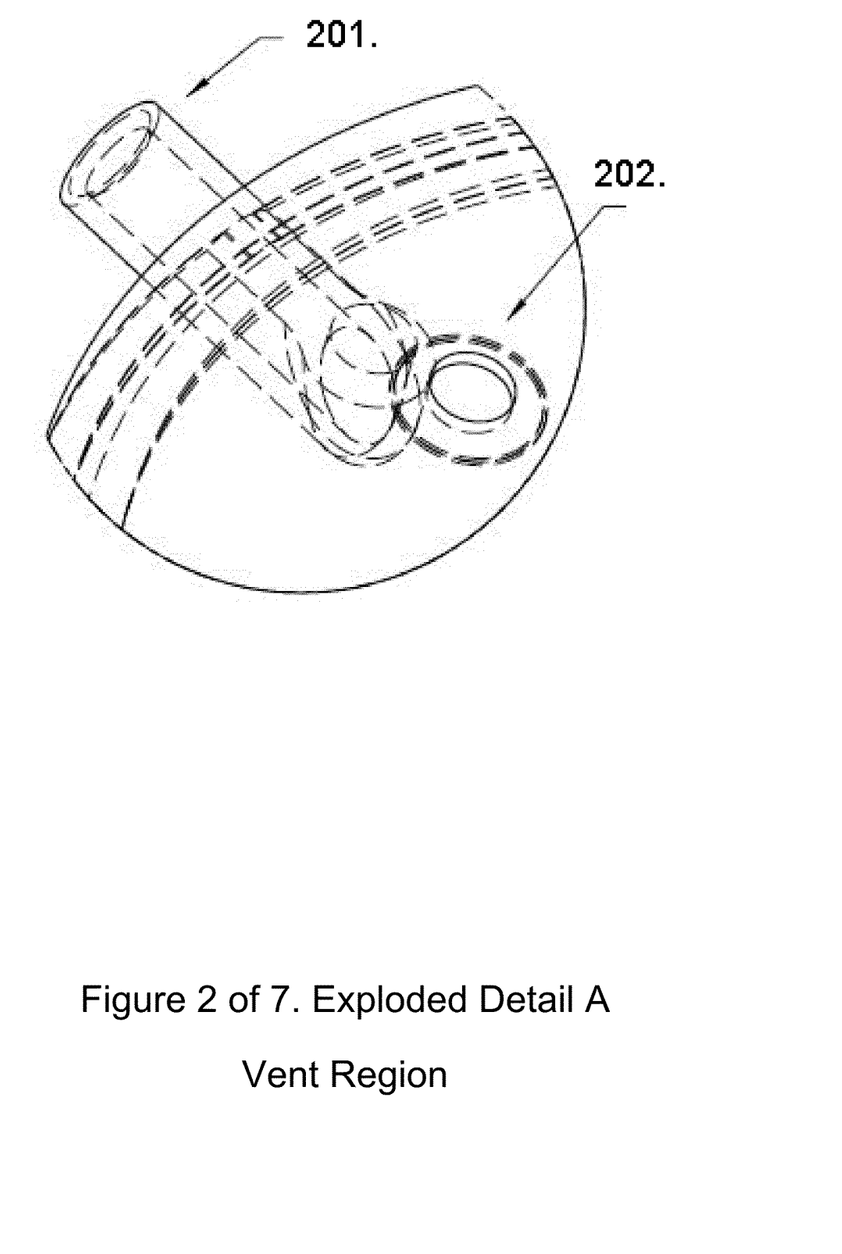
FIG. 2 is an exploded view looking through the device of the Vent Region identified by (A) in FIG. 1.
Figure 3:
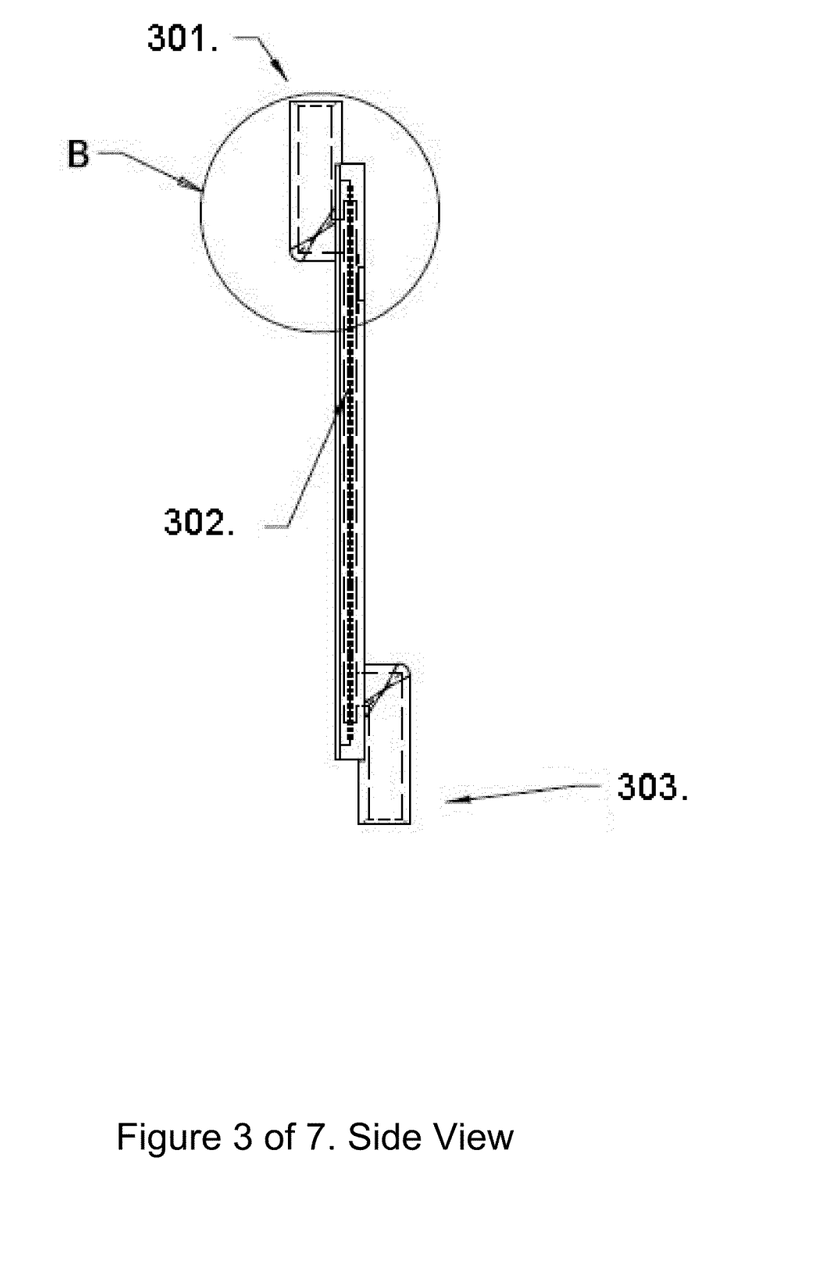
FIG. 3 is a cross-section view of the FIG. 1 exemplary vented cartridge filter showing the relationship of the fluid inlet port (303) and outlet port (301) in communication with their respective inlet and outlet chambers. The porous filter membrane (302) held between the inlet and outlet-chambers, through which fluid flows for the filtration, is identified.
Figure 4:
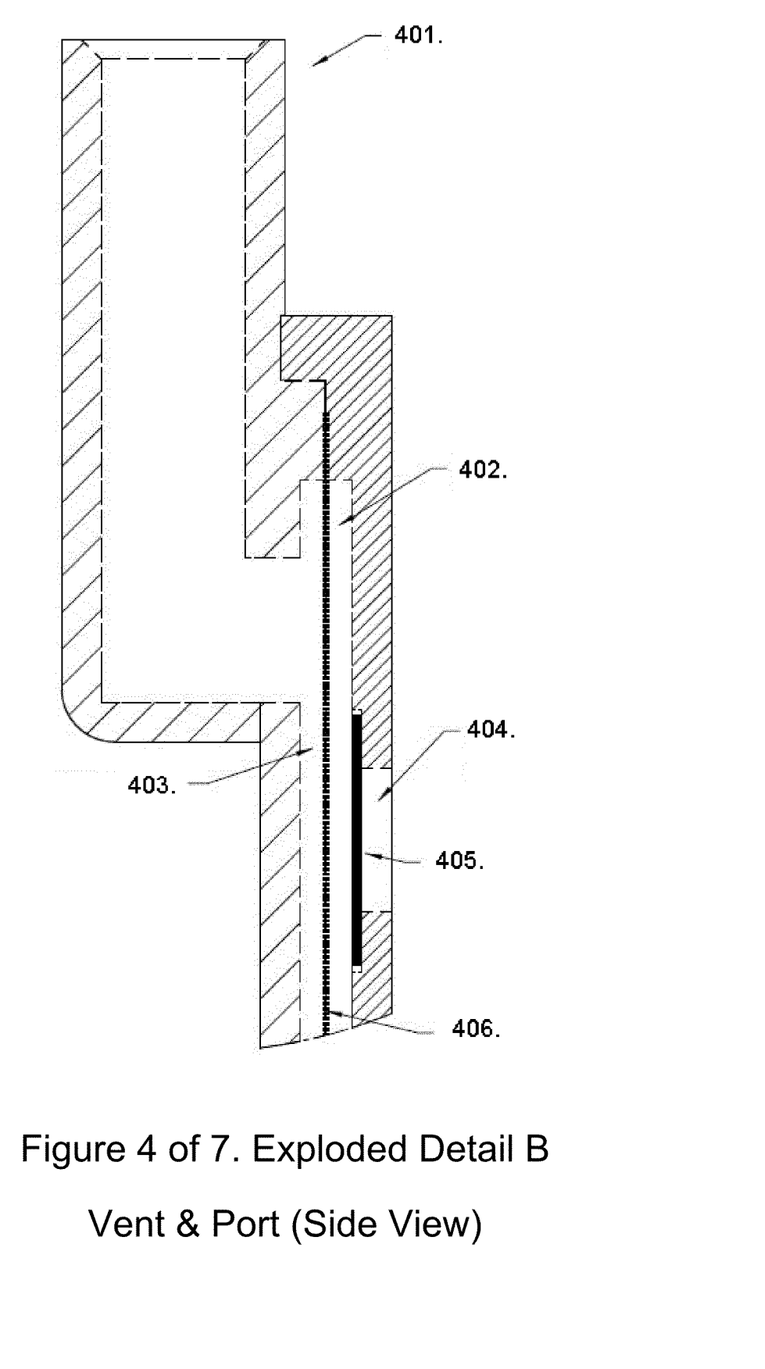
FIG. 4 is an exploded view looking through the Vent Region identified by (B) in FIG. 3.

A schematic representation of an exemplary vented-cartridge-filter (VCF) is shown in FIGS. 1 through 4. A preferred design is a flat clear plastic cartridge with a fluid inlet-port on one end leading to a inlet chamber of small-volume. A hydrophilic porous filter membrane (302) is sandwiched between the inlet chamber and a similarly small-volume outlet chamber with a corresponding outlet port (301) (FIG. 3). Schematic details of the vent region are shown in the exploded views of FIGS. 2 and 4.

We found that by applying active suction, negative pressure, to the vent of commercial IV-filters of the type described (e.g., Pall "Micro_IV" filter, Filtertek "Micro-Infusion" filter, Borla "Vented Pediatric" filter), the vacuum thereby created in the inlet chamber more quickly and efficiently filled the apparatus with fluid, in contrast to a gravity-feed operation. Fluid was actively drawn into the chamber. A rapidly advancing fluid-front had fewer tendencies to form air pockets or leave residual air trapped in the chamber. The negative pressure was applied using a simple vacuum bulb or suction-cup type device placed over the vent. Alternatively, a suction cup attached to a vacuum source of more capacity was used if large quantities of air needed purging from the filter apparatus. In either case, after the fluid filled the chamber and reached the vent, it blocked the vent, which it cannot pass through, thereby effectively stopping the suction.

The constraint of using positive pressure fluid delivery systems puts limitations on the manner and scope of VCF use. It is not always desirable or practical to push fluid from the upstream side of the filter into the VCF. The approach can also have other deficiencies in terms of dynamics of fluid flow inside the VCF inlet chamber, efficacy of getting air completely purged out via the device vent, and achieving optimal filtration performance.

We discovered with the inventive method that these deficiencies can be overcome and several advantages towards filtration processing fluids provided, in particular enabling practical uses of negative pressure or vacuum based filtration with VCF. This opens up new opportunities for VCF applications. The key innovation relates to the application of negative-pressure to the inlet chamber vent in order to actively pull air out of the VCF.

As indicated, applying a vacuum at the vent creates suction within the inlet chamber enabling fluid to be pulled into the inlet chamber via the inlet port. We found, moreover, that vent suction applied to either a dry or wetted VCF, could be used to lift fluid from a vessel against gravity and pull it considerable distances through a fluid path to the VCF. Vent suction furthermore provided utility for aspirating very small amounts of fluid mixed with large quantities of air through an inlet path, e.g., pulling residual drops from the bottom of a vessel. Active negative pressure applied at the vent was sufficient to efficiently and completely fill the inlet chamber of different VCF of various configurations without any positive-pressure assistance to fluid flow on the inlet path.

Hence, with the inlet chamber filled with fluid (not air locked) and covering the filter membrane, the fluid was drawn through the filter, i.e., filtered, by negative pressure applied on the outlet side of the filter. Namely, with a vacuum line attached to the inlet-chamber vent and a vacuum line attached to the fluid-path outlet port on the outlet chamber of an IV-filter VCF, we established that: filtration was initiated with a dry VCF; or readily re-initiated with a previously wetted VCF; and furthermore, filtration was repeatedly restored with VCFs that were intermittently exposed to large boluses of air that filled the VCFs.

Summarily, we demonstrated that a vacuum applied to an inlet-chamber vent, preferably continuously, enabled vacuum to be utilized as the practical basis for aspirating fluid and/or air into VCF and performing filtration of said fluid(s) with VCF in a controlled stepwise manner, without requiring a positive-pressure pump or gravity-fed fluid delivery system to push fluid into the VCF.

To further implement this, an innovative vacuum tool was designed for use with VCF devices. This tool provided for both the attachment of a vacuum line to the vent on the inlet chamber of the VCF (vent suction), and a vacuum on the outlet port to conduct the fluid filtration (fluid suction).

Figure 5:
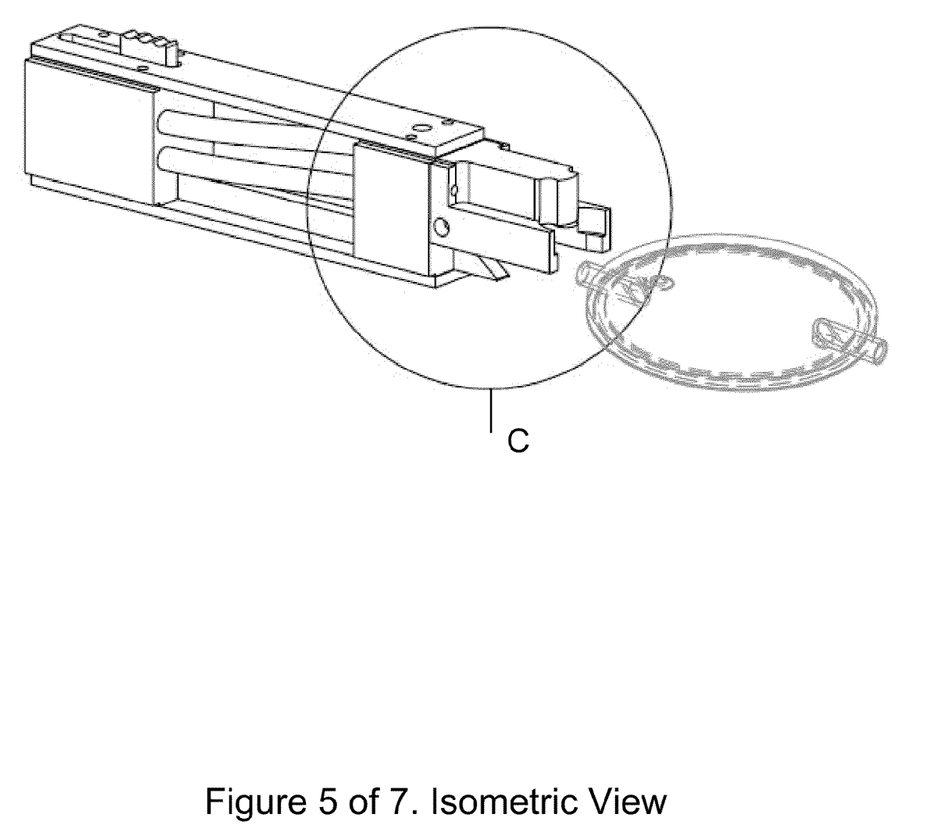
FIG. 5 shows one version of a Vacuum-Tool to illustrate in overview the relationship between the tool and a vented cartridge filter (such as represented in FIG. 1), which would mate with the tool. The tool has two vacuum lines in it running to the filter receiving head-piece: one serves as the fluid suction line; the other serves to draw air out through the filter's vent.
Figure 6:
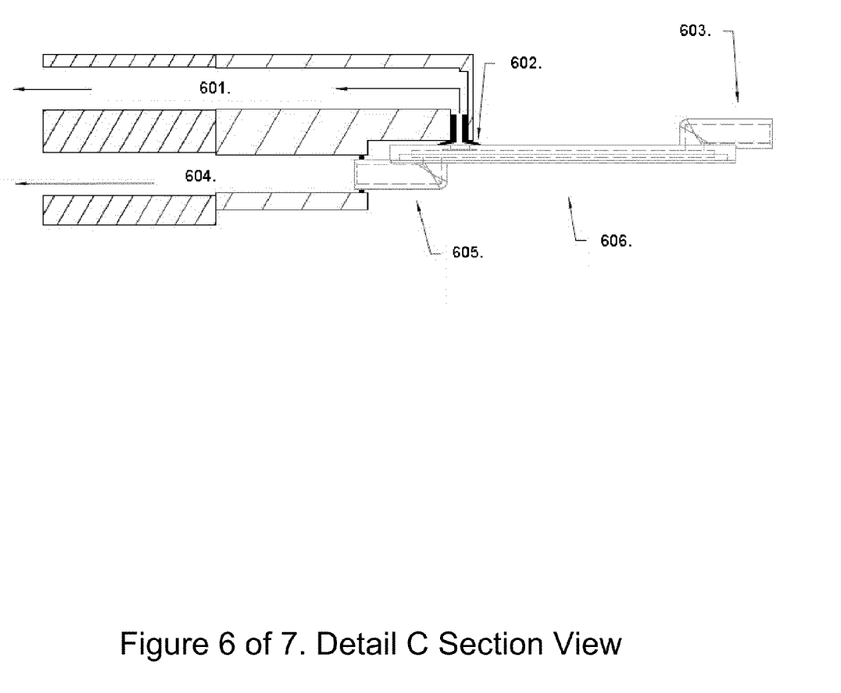
FIG. 6 is a cross-section view of the exploded region (C) of FIG. 5 showing the Vacuum-Tool head-piece with a vented cartridge filter (606) mated to it as would be used in a filtration application. It illustrates the tool's fluid suction line (604) mated with the fluid outlet port (605) of the VCF (a seal effected between the two components). It also shows the tool's air suction line (601) mating with the vent on the VCF's inlet chamber side. A cuff (602) at the end of the tool's air suction line for making a convenient seal with the VCF vent is also illustrated. Also pictured is fluid inlet port (603).

A version of a vacuum tool is shown in FIG. 5. An exploded view of the head of the tool with a VCF attached is shown in FIG. 6. A vacuum source line applied to the tool is split into two branch lines in the tool. The main branch (504) attaches to the filter-cartridge's outlet port (505). It serves as the suction line for pulling fluid through the filter membrane, out the outlet chamber port, and conveying it away for dispensation.

The second branch line (501) is for vent suction. It connects to the vent on the filter's inlet chamber. A soft rubber cuff (502) provides an effective suction-seal with the cartridge housing. The second suction line to the filter vent provides the important advantage of pulling air out of the cartridge's inlet chamber, sucking fluid into it, and filling the inlet chamber with fluid so that fluid filtration can proceed without air locks.

It was advantageous to also incorporate adjustable valves into the vacuum tool for controlling the vacuum to the vent suction line, and regulating fluid vacuum and flow at the fluid line. A control valve on the fluid filtration line was particularly useful. It allowed the filtration process to be stopped, started, or the flow rate increased or decreased at any time. It provided unique advantages in terms of efficiency of sample preparation with respect to purging and rinsing the cartridge and consistently filling it uniformly for assay using minimal volumes of reagents.

In summary, the method and vacuum tool described providing for application of vacuum to the inlet-chamber vent as well as the outlet chamber fluid port enables:
  Elimination of air bubbles and preventing "air-locks" in the VCF as the result of air getting into the inlet fluid path either inadvertently or intentionally.
  Evacuating air quickly and completely from the VCF inlet chamber.
  Aspiration of fluid through a fluid path to the VCF and filling of the inlet chamber.
  Enabling vacuum to be employed at the outlet side of the filter for drawing fluid through the filter element.
  Eliminating the constraint of VCF use with only positive-pressure fluid delivery systems.
    To be noted, either negative pressure or positive pressure based fluid filtration systems can be used with the VCF and the inventive method.

With respect to a specific category of filtration, we draw reference in the field of microbiology to a classic analytical technique called the membrane filtration (MF) assay. It is one of the most commonly practiced laboratory assays. MF is employed when it is necessary to obtain outgrowth of discrete colonies in order to identify bacterial types present, or when the enumeration and quantification of bacteria in a fluid sample is essential to the assay. It is an important tool for harvesting organisms from a volume of fluid, and concentrating them on a filter, where they can then be cultured and grown into colonies for analysis. MF is also used in related manners for conducting diverse types of cellular assays in other disciplines as well.

MF is widely used across industries spanning medical, food and beverage, to water and environmental testing. It is estimated that several hundred million MF related tests are performed annually. Assays typically use 25 to 47 mm diameter filter membranes made from a wide variety of microporous materials such as mixed-cellulose ester, polyether sulfone, PVDF, or nylon. Most microbial assays are conducted on "depth" filters of 0.45 or 0.2 micron pore structure, which is small enough to capture most all bacteria.

The typical approach for preparing a MF assay sample consists of locking a sterile membrane filter disk between the two-pieces of a filter funnel apparatus. The top piece is an open wide-mouth funnel reservoir of sufficient volume to hold the parent fluid containing the bacterial sample of test. A base portion holds the filter membrane and supports it on a solid mesh grid to prevent rupture when fluid is pulled through it. The sample fluid is poured into the funnel reservoir and drawn down through the filter via vacuum applied beneath the membrane. The reservoir and the filter are then washed with a rinse fluid. The apparatus is disassembled, the membrane removed from the base support, and then carefully transferred to a secondary culture vessel. The culture vessel is typically a petri dish containing either a solid agar substrate or an absorbent pad saturated with liquid culture media onto which the filter is laid.

The classic filter-funnel approach described has been widely used for decades as a primary means to harvest bacterial samples, despite its considerable disadvantages. The sterile membrane is significantly exposed to air and the external environment during the procedures and membrane transfers operations, thus has an attendant risk of getting contaminated. The safest practice is to perform sample preparation in a clean laboratory environment or in a protected microbiological hood, which consequently constrains the situations and setting where the assay is conducted.

Another problem is cross-contamination between sequentially prepared samples. When more than one sample is to be filter processed, the first test fluid will contaminate the holding reservoir. A different sterile reservoir should be used, one for each sample, or alternatively the unit should be decontaminated between every sample usage. This involves more procedural labor, such as performing a UV treatment, flame, or chemical disinfection and rinsing, none of which are without risks of potentially compromising the subsequent sample run.

An additional shortcoming is after the filtration process, for the membrane's culture phase additional assay materials (e.g., petri dishes) are needed to receive the filters. This involves making or procuring poured agar media plates. Alternatively culture dishes have to be prepared with absorbent pads saturated with a specific volume of culture media dispensed into the pad, e.g., Millipore PetriSlides™. The pad serves, like agar, as a means of holding and supplying nutrients for culturing the cells. The membrane filter with the captured cells then has to be manually conveyed to the culture vessel, without contaminating it, and laid on the feeder layer of agar or the pad.

In short, the classic MF assay with a filter-funnel approach requires a lot of materials and time to prepare the hardware, filter the sample, get it into culture. It is labor intensive, cumbersome, and has contamination risks. It is best performed in a well equipped, carefully controlled clean lab environment.

For convenience and labor saving, various disposable one-time-use filtration assay devices have been marketed, e.g., Millipore Microfil™, Whatman Monitor™, and Nalgene Filter-funnels. As renditions on the filter-funnel theme, these generally have a large volume plastic funnel reservoir and a base unit pre-loaded with a filter membrane. Their parts disassemble permitting user access to the membrane in different manners. Being dedicated single-sample use devices they eliminate concern over cross contamination between samples via the funnel.

They are not without shortcomings. Most still adopt the wide open large reservoir on top to receive the fluid sample, which is subject to contamination. Typically, a membrane transfer to another culture vessel is still required, with its attendant cost. For the convenience of the disposable plastic device the price is a high unit cost and disposal issues.

These membrane-filter assay applications share common need for the filtered sample to be protected from the environment. There is need for simpler sample preparation procedures, avoiding the transfer of the membranes, and eliminating the risks of sample cross-contamination. There would also be distinct benefits through combining the functions of the filtration device to also be the culture vessel and assay vessel.

These objectives could all be met using encapsulated filter apparatuses adapted into self-contained protected multifunctional filter-concentrator-culture vessel-assay devices; but heretofore such a model was flawed. The aforementioned problem of air getting in the fluid path and interfering with or blocking fluid flow has been an impediment to sample preparation. Introduction of air is practically unavoidable in typical assay setup procedures, especially when passing finite volumes of several fluids through the encapsulated device: e.g., sample, rinse fluid, culture media, and/or test reagents.

The inventive method and device is a major achievement because it eliminates this barrier to implementation with enclosed VCF. Moreover, it enables the use of negative pressure of vacuum on the fluid path to perform the filtration.

The enablements of the inventive method and device for practical applications of VCF, and specifically for in vitro assays of sample testing by MF, include:

A compact, enclosed, protected, aspiration and filtration system, with minimized risk of exposure and contamination of the sample, or the user.

For using VCF, to serve in addition to filtration, as a vessel for culture and/or assay of the contents.

For fluid processing utilizing negative pressure, vacuum-based fluid filtration, or alternatively positive pressure approaches.

For filtration and concentration of matter from large volume samples into a compact VCF.

For aspirating fluids or pulling solutions conveniently from vessels, even working against gravity, and filter processing the sample through the VCF.

For using air drawn into the VCF to interrupt fluid filtration, then resuming flow to reinitiate filtration.

For performing convenient stepwise sample processing, for instance, first filtering test fluid, then rinse fluid, and finally media aspiration.

For conservatively using small volumes of media or reagents.

Eliminating dependency on positive-pressure fluid delivery avoids complications with equipment and fluid path materials needed on the inlet side that become contaminated with contact of each separate fluid sample. For sequential preparation of multiple samples, the risks of cross-contaminating samples following one another can be avoided using negative-pressure fluid filtration approaches. This means less contaminated material is generated to dispose of or decontaminate.

The following is a detailed example of the use of the inventive method and a device to prepare filtered water samples in a vented encapsulated filter apparatus for a Membrane-Filter based analysis of the bacterial contaminants of sample water.

The following describes the main sample filtration process:
1. A vented-filter was attached to a vacuum tool such as shown in FIG. 5. The two vacuum lines within the tool were mated to the VCF air vent and the outlet port for fluid suction.
2. Negative-pressure was applied to the vent.
3. The filter's inlet port (or a tubing connected to the port to act as a pick-up extension) was immersed in the sample fluid. Fluid was immediately sucked up into the cartridge filling the inlet chamber. It was preferable to completely cover or bathe the filter element with fluid in order to attain maximal utilization of the surface area of the element as well as a desirable dispersion of the harvested particulate over its surface.
4. The sample was filtered by the suction via the fluid-vacuum line applied to the outlet port until the desired volume of fluid was processed. At that point the sample acquisition was complete.
5. It was of distinct advantage that the sample aspiration and volume of fluid filtered could be limited in several manners. One was to stop the fluid-vacuum, which terminated filtration. A second was to remove the vacuum from the vent allowing air to be drawn into the VCF and create an air lock to stop flow. Another was to allow the filtration to proceed until all of the fluid made available for aspiration was filter processed (e.g., a predefined volume in a vessel). A fourth was to withdraw the VCF inlet port or inlet pick-up tube extension from the sample fluid after the appropriate volume had been filtered.
    1) A preferred rendition of the latter approach, particularly advantageous for limiting the volume of fluid filtered to a certain amount, was to use a pick-up extension tube affixed to the filter inlet port such that when inserted and immersed in a vessel of fluid it reached to a consistent depth. Thereby, from vessels of consistent type and filled to a consistent volume or level, a consistent defined sample volume was aspirated from the fluid vessel and filtered. The fluid flow was terminated when the fluid level in the vessel dropped below the inlet of the pick-up and air was drawn into the filter inlet chamber.
6. It was an advantage that is was not absolutely necessary to terminate vacuum to the fluid path when the end of the fluid sample was reached. Whenever air filled the inlet chamber creating an air-lock condition, intentionally or unintentionally, fluid flow in the VCF essentially stopped automatically. That left the VCF in a desirable state of having a wetted membrane, and an outlet chamber filled with fluid. To conduct steps of rinsing of the filtered sample, the following was most efficient.
7. After the desired amount of sample fluid was filtered, the VCF inlet port (or tubing) was exposed to air while the VCF was still under vacuum at the fluid line. Suction drew all fluid into the inlet chamber and through the filter membrane. It purged the inlet chamber and voided it with air. The outlet chamber, however, remained filled with filtered sample water because of the air lock on the inlet side of the VCF.
8. The vacuum to the fluid-line was then briefly closed with a valve to temporarily prevent filtration.
9. The VCF inlet was then introduced to a rinse solution. The suction at the vent drew the fluid into the inlet chamber, filling it, and uniformly bathing the filter membrane in the rinse.
10. The fluid-line vacuum was then reopened. Resumption of that suction pulled the rinse solution through the filter membrane. The approach thereby had the important practical benefit of ensuring complete homogeneous exposure of the membrane to the rinse. The rinse solution drawn into the outlet chamber also displaced the residual sample fluid that was in the outlet chamber and flushed it out the outlet port.
11. To maximize flushing of residual sample fluid remaining in the inlet or outlet chambers or the membrane, repetitive cycles of the rinsing process described were performed: voiding the inlet chamber with air, refilling the inlet path with rinse, pulling it through the filter, and flushing of the outlet chamber. Rinsing was conducted alternatively with one continuous draw of rinse through the VCF with an uninterrupted flow. However, we found that the latter was less efficient in terms of flushing away residual sample fluid and conserving the amount of rinse reagent used.

The following were performed to administer media to the VCF and initiate culture and assay of the filtered contents:
12. The procedure for administering a cell-culture medium or other reagent to the VCF was the same as described for the rinse. Our finding was that it was more efficient and conservative of reagent to perform the operation as described before in several cycles of the inlet air-purging, refilling, and flushing. The use of valves to manipulate the timing and where vacuum was applied to the VCF was extremely valuable, essential for conducting the operations efficiently.
13. Using the procedure described, valves provide definitive control over the operation. For instance, when there was only vacuum applied to the vent, precisely the amount of fluid "charge" needed to fill only the inlet chamber was pulled into the VCF. This was varied by simply changing the length of inlet tubing attached to the inlet port, which could be regarded as an extension of the inlet chamber and thereby defining the inlet-path volume.
14. Also used to advantage was air-locking of the VCF filter membrane when all fluid was pulled from the inlet side. It made part of the operation self-regulating from the standpoint that flow automatically stopped after all of the fluid available to the inlet path was drawn through the filter element. Yet the filter element remained wetted.
15. To complete the process, for culture of the membrane-filter captured cells, after flushing and filling the VCF with media, either of two procedures were used:
    1) In one case the VCF was removed from the vacuum tool while in a condition having media filling both the inlet and outlet chambers. The inlet and outlet ports were plugged or covered to prevent media leaking out and to minimize exposure of the contents to external contaminates. The media-filled VCF was incubated in that state, with media surrounding the cells, to promote their outgrowth.
    2) The alternative procedure was to perform a final air purge of the VCF inlet chamber using suction from the fluid line to remove the fluid from the inlet chamber. The cartridge was removed from the vacuum tool with the membrane wetted and the outlet chamber filled with media. Its inlet and outlet ports were plugged or capped, and the VCF put in an incubator to begin the culture phase.
16. The vent opening with either of the above two approaches was alternatively left open, or covered, depending upon assay application preferences. Its hydrophobic membrane protected the sample in either case from exposure to external microbial contaminants The manner of microbial assay setup that left only the outlet chamber filled with media and the inlet chamber filled with air, enabled discrete colonies to grow on the surface of the filter membrane. The colonies were fed by the culture media in the outlet chamber which was in direct contact with the membrane. The colonies growing on the membrane were visually analyzed, scored, and counted in the same manner as the current convention of MF based assays.

The mode of application, to obtain outgrowths of colonies, is thus highly analogous to classic techniques for MF based enumeration assays. The VCF culture condition described in fact may provide an advantage to cell growth. By comparison, the conventional media pads and agar based substrates used in culture vessels for membrane-filter assays inherently have constraints on nutrient diffusion through the pad or the agar matrix. This is not the case per our described procedure in which the membrane in the VCF is in direct contact with the culture media fluid feeding the cells.

In our other mode of media administration, for culturing the VCF when the cartridge was completely filled with media (inlet chamber not air-purged), the organisms were completely surrounded or bathed in media. That enabled their culture and outgrowth in a planktonic mode, able to dissociate from the membrane, disperse, and grow freely in suspension in the media. That scenario mimicked the assay environment of a liquid broth or tube-based culture condition.

We have established that sample filtrations using the described procedures are quite practical with vented cartridge filters and a vacuum-tool applying suction in the manners described. Fluid samples were processed with no concern over air getting in the fluid path, or air-locks preventing flow and terminating filter use or sample preparation. In fact, flow was intentionally interrupted using air. Air-purging of the inlet chamber was used to distinct advantage.

The preparative procedure is fast and efficient. Using small vented medical IV-filters containing ~15 mm diameter membranes of 0.8 u pore polyether sulfone, 100 cc water samples were filtered in under one minute. The entire process of sample preparation for MF assay from the start of filtration through rinsing, media administration, and into incubation was completed in less than 90 seconds total processing time. By comparison, using a conventional funnel-filter with a larger 47 mm diameter membrane of the same type, though having a faster filtration rate, the total preparation time for getting the filter into a petri dish and ready for culture took longer.

The use of the vacuum-tool and the vent suction technique enables highly efficient flushing and presentation of media or other reagents uniformly throughout the filter-cartridge, maximizing flushing and rinsing. As an example of conserving resources, in the case of the IV-filters with 15 mm membranes, only a small 125 microliter aliquot of media was required to completely fill the inlet chamber and cover the entire membrane. With 0.5 ml of media, the VCF could be media-flushed several times and made ready for assay.

The air vent itself provides an important function with respect to assays and cell culture or growth conducted within the VCF in an incubation step. The vent allows gas exchange, in and out of the enclosure. Cell growth of some organisms significantly benefit from having an avenue for gases, such as carbon dioxide or ammonia to escape from of the culture vessel. Oxygen ingress into the culture environment in many cases is also significantly beneficial to growth. In some cases, it is preferable to cover or plug the vent to prevent gas exchange, e.g., to limit oxygen availability. There is distinct advantage to having the vent present, with the option to either leave it open or close it, depending upon the application preference.

Since the sample in the VCF is well protected from external contamination during setup and assay, it is an excellent candidate for sample preparation in austere settings, such as remote field uses, or in small labs and other facilities, i.e., less than ideal lab conditions.

An additional advantage of the system has been identified when dealing with bacteria. Since the VCF captures the bacteria from the fluid passed through it, the filtered fluid on the outlet side of the system with the bacteria removed is clean. Thereby, risks of a cross-contamination between samples, via contact of a VCF outlet port and the vacuum tool, are minimized. Moreover decontamination and clean-up issues related to the tool and vacuum system are minimal.

Utilization of the inventive method and device towards preparation of membrane-filtered fluid will aid sample throughput in large labs and testing facilities processing multiple samples per day. Since either a large or small volume of fluid can be drawn out of a sample vessel into a relatively small discrete filter-cartridge, the system is well suited for adaptation to automated or semi-automated sample-processing work stations. For example, with planar filter-cartridges (circa 50 mm diameter×10 mm thick) inserted in vacuum-tool heads positioned above sample vessels, the work station could lower the VCFs to the vessels, withdraw and filter the required samples, then retract. The VCF could then be moved to other vessels in order to pull up media, rinse fluids, or other reagents.

A further innovation applicable to the use of the inventive filtration method and device is the implementation of a "volume-limiting" filtrate collection vessel on the outlet side of the filter apparatus. This special adaptation is designed to control and limit the volume of a sample fluid that is processed through the filter. It addresses an important need in some applications, such as the membrane-filter microbial assays, for discrete defined volume(s) of sample fluid to be filtered consistently from one sample to the next, e.g. 100 cc.

This is accomplished by incorporating a vented or valved filtrate-collection chamber in the fluid outlet or discharge path of the filter such that only a finite defined volume of sample fluid passes through the filter. After the prescribed volume of sample filtrate is acquired in the collection chamber, the fluid path becomes blocked preventing further fluid flow through the VCF upstream.

Figure 7:
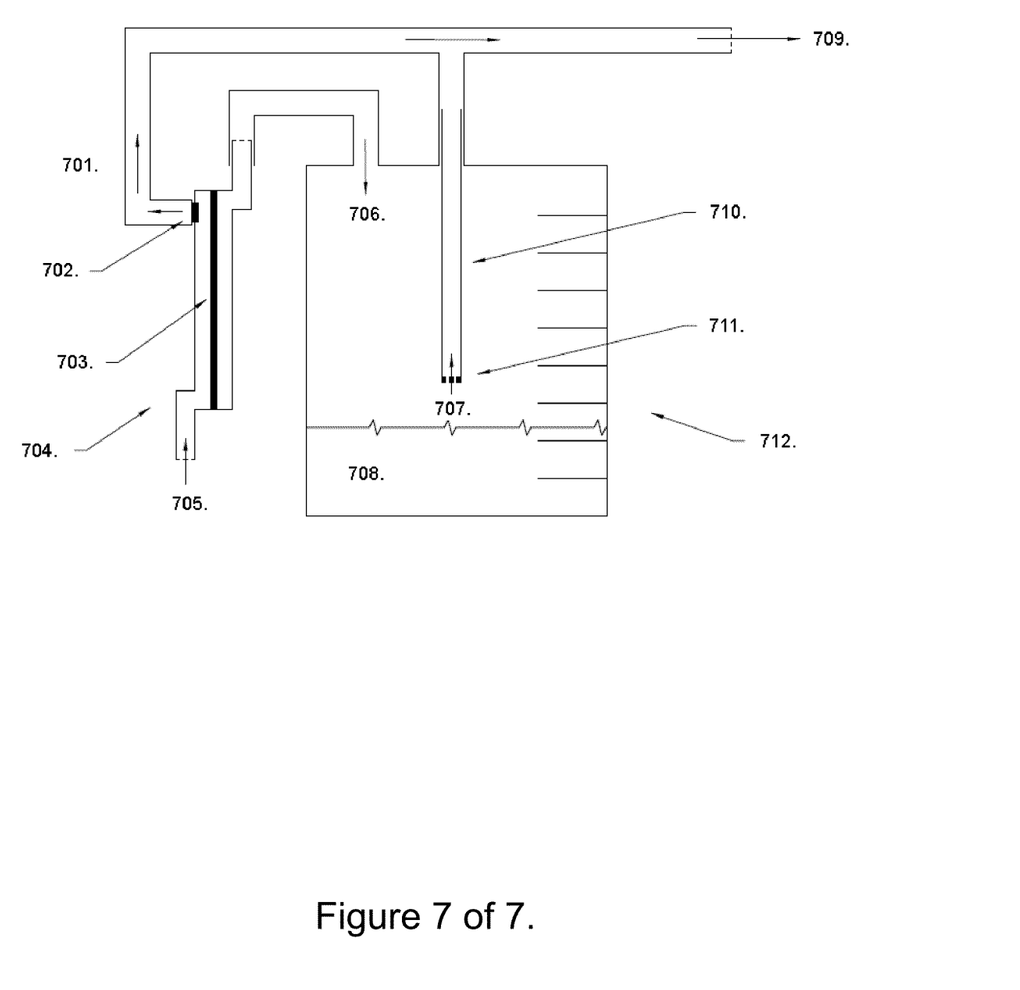
FIG. 7 illustrates one example of a "volume-limiting means" or controlled-volume filtrate collection chamber for use with a Vacuum-Tool and a VCF. The schematic shows the flow-path of fluid and air for the collection chamber (712) and an attached VCF (704). An adjustable air-vent tube (710) with a porous hydrophobic material (711) over the vent hole is identified through which suction is applied to the collection chamber causing fluid to be drawn into the collection chamber connected to the outlet port of the VCF. Additional drawing elements: Vent Suction (701); Porous Hydrophobic Material (702); Hydrophilic Filter (703); Air and Fluid Inlet (705); Fluid Inlet (706); Air Outlet (707); Fluid (708); Vacuum Source (709).

One rendition of a controlled-volume collection apparatus that uses an air-vent based fluid control mechanism is shown in FIG. 7. The operative principle is similar to that of the air vent of the VCF. A hydrophobic porous vent (711) incorporated into the collection chamber (712), passing air but not fluid, enables a vacuum to be applied to the chamber via the fluid-vacuum line (709). The vacuum at the vent creates suction in the chamber thereby causing fluid, filtrate, to be pulled through the VCF (704) into the chamber. When the collected fluid level rises in the chamber and reaches the air vent (711), the vent becomes blocked. Suction stops and filtration is terminated since air is no longer pulled out of the chamber and the fluid is unable to pass through the vent.

To create a fixed fluid-volume collection chamber, a hydrophobic vent can be built into the top of the chamber of specified volume. The vent can also be incorporated at a specified level or height, for instance, into the side of chamber in order to achieve a specified holding-volume limit. Many collection chamber designs are possible. The essential property is that the vent be placed such that the fluid level, with the desired volume of filtrate collected, occludes the vent.

Alternatively, as shown in FIG. 7, by placing the vent (711) in an adjustable tube (710) inside the collection chamber (712), the tube or vent position can be moved in order to reach different levels within the chamber. The position of the adjustment tube thereby defines the volume of fluid that will be collected in the chamber. Vacuum pulls sample fluid through the filter (703) until the filtrate fluid level rises in the collection chamber to the hydrophobic membrane on the adjustment tube. At that point, suction through the adjustment tube is blocked, yielding a precise and repeatable amount of fluid filtration.

Other valve or fluid control mechanisms can be implemented to achieve the same objective of limiting the volume of filtrate processed/collected. For instance, a float-type arrangement could be used to terminate flow, using such as a floating ball-in-a-tube, or a floating membrane flap that rises with the fluid level, ultimately occluding the vent, acting as a shutoff valve.

After the defined volume of sample has been filtered, implementation of the controlled-volume chamber can include provisions for subsequent delivery of rinse solution, media or reagent through the filter. To filter additional fluid, for instance: the collection chamber could be bypassed, removed or voided of some of its fluid; the suction adjustment-tube could be repositioned; or the apparatus could simply be reoriented to re-expose the vent to residual air within the chamber.

The controlled-volume chamber innovation provides important advantages. It enables consistent defined volumes of sample fluid to be reproducibly filtered in a convenient manner. It minimizes operator involvement or intervention to control and limit the filtration. It eliminates the need to control the sample filtration based on restricting the fluid volume presented to the filter apparatus on the inlet side of the fluid path.

By eliminating the latter need for controlling or limiting the fluid volume presented to the filter apparatus on the inlet side of the fluid path, several important benefits are gained. It eliminates the need for equipment and articles to measure out the required sample volume and a separate holding vessel from which it is drawn into the filter (e.g., the filter-funnel reservoir for MF sample preparations).

Complications associated with sample contamination are reduced by avoiding fluid handling and processing aids, fluid-path tubing, and fluid-holding vessels for presentation to the filter apparatus inlet path. The risks of cross-contamination between sequentially prepared samples, and the alternative problems associated with preparing each sample using new or decontaminated articles, are also avoided.

Overall, the sample preparation procedures using the VCF, vacuum based filtration, and the controlled volume apparatus are enablements that greatly reduce or eliminate the need for pumps, positive pressure fluid feeds, and fluid handling or transfer materials on the upstream side of the filter membrane for the preparation of filtered samples. These improvements make practical and economically attractive the use of enclosed cartridge filters as self contained combined filter and assay device. Moreover, the feature set achieved makes the new fluid filtration system highly attractive to fully or semi-automated sample preparation systems based on the use of encapsulated filter cartridges.

With respect to the design of the VCF and the use of this invention, the vent on the VCF can simply be an open hole or passageway in the inlet chamber where negative pressure is applied to evacuate the chamber. The vent size and location, as well as other VCF design parameters, such as the filter configuration, inlet and outlet chamber sizes and configurations, and amount of vacuum applied to the vent relative to the rate of fluid filtration, are variables that can be specified to meet particular application-specific requirements.

For instance, the inlet chamber could have an open vent hole located a significant distance above the level of the filter element to ensure that fluid drawn into the chamber first covers the filter element in whole or in part (as in FIG. 3, with the orientation shown). The amount of vent vacuum relative to the filtration rate could be adjusted so that the fluid level in the inlet chamber does not rise to the level of the vent. Fluid in the chamber would thus not be aspirated out the open vent.

There are advantages to having the vent covered with a restrictive device that prevents fluid from being sucked out of the vent, such as the porous hydrophobic membrane of previous example. Various materials can be used as a vent cover that provide the basic function of allowing passage of gas, but not fluid, e.g., Teflon, PVDF, silicone. Other approaches to achieve the same objective can also be employed that do not employ porous or gas-transfer membrane. A floating flap or ball, for instance, can be used as a valve that blocks the vent passage when the fluid rises in the inlet chamber to the level of the vent.

Rather than incorporating a vent-restrictor into the VCF, another alternative is to incorporate the equivalent functionality into the vacuum tool. For example, porous hydrophobic material integrated into the end of the tool at the point where it mates with the VCF vent stops the vacuum when the fluid reaches the tool and blocks the vacuum pathway. The operative principal is analogous to using the restrictive membrane in the VCF as a barrier to fluid flow.

Various additional types of applications are envisioned for using enclosed-filters which capitalize on the suction to the vent. An aforementioned application is to use just a suction device applied to the vent of a VCF, such as the medical IV filters. The tool would simply apply negative pressure to the filter's vent in order to help keep air out without relying on positive fluid pressure. It would help ensure the filter performs with optimum flow and efficiency.

It is to be noted that this invention is not limited to use with filtration devices for aqueous fluids and porous hydrophilic membrane based filter-elements that physically separate material based on size. The advantages offered by the invention are applicable to other types of membranes, as well as filter elements that are not membranes, and that work on different filtration principals such as chemical bonding or charge-based reactions.

The invention should more generally be regarded as applicable to devices where: a material is confined and/or enclosed, in a cartridge or housing requiring fluid to be passed through it, but air will be expected as well to enter the device, which at times will adversely affect the performance of the device, and therefore the device should be provided with means to remove or exclude the air as necessary.

An example is a cartridge containing a matrix that chemically absorbs or immuno-chemically bonds constituents from a fluid that passes over the matrix. Utility of the cartridge, as a filtering device, and more specifically as an assay device, would benefit from application of the described invention to achieve basic objectives of: evacuating air from the cartridge, aspirating or pulling fluid(s) into the filtration apparatus, eliminating complications from air entering the cartridge, and enabling fluid flow-through.

Moreover, it can be appreciated that application of the invention is not limited to removal of air from an aqueous fluid. The inventive principal is likewise applicable to removing, for instance, unwanted fluid that enters into an enclosed air filtration device. In such a case, per the examples previously given, the filter element of choice would be, for instance, a hydrophobic porous material to pass air and not fluid, and the vent employ a hydrophilic porous membrane to pass only the fluid.

It is further anticipated that by similar principal of operation the invention can be applied to a vented-cartridge "filter" serving in the general capacity of a separation device. For example, two immiscible fluids, e.g., oil and water could be separated with the active removal of one from an enclosed cartridge via a vent using the invention. Membranes having selective properties chosen to separate and pass or not pass the respective fluids would be employed.

With respect to the fundamental objective of actively creating negative pressure in an inlet chamber of an enclosed cartridge device, the heretofore described application of vacuum via a vent is not the only possible approach. One alternative is to produce a negative-pressure within by having a movable element incorporated into the inlet chamber. By pulling the movable element to cause the internal volume of the chamber to increase, a negative-pressure is created. The movable element could consist of a sliding portion of the inlet chamber, or a flexible membrane that is distorted to increase the chamber volume.

In regard to preferable examples of the VCF, for assay applications such as the enumeration of bacterial colonies cultured on the surface of a membrane filter, desirable VCF properties are as follows. A cartridge having a clear housing, preferably plastic, with an unobstructed window or viewing area which can be used to visually discern or optically interrogate the surface of the filter membrane for signs of organism growth. Preferably the filter membrane has a surface area for capture and culture of organisms of between approximately 2 and 25 square centimeters. Preferably the total volume of the cartridges, inlet and outlet chambers, is as small as possible to minimize device size and particularly the volume of reagents or media needed for conducting assays, e.g., total volume of between 0.2 and 5 milliliters. Preferably the cartridge is provided with a removable lid or cover such that the contents can be accessed, for instance, to extricate a sample of organisms growing on the filter membrane for subsequent examinations. The fluid flow across the surface of the filter membrane and filtration through it should be sufficiently homogeneous to provide for uniform dispersion and deposition of matter in the fluid, including cells, over the membrane surface. The cartridge preferably provides for optional venting, gas exchange, of the contents to promote efficient growth of organisms contained therein.

To be noted with respect to a separable cartridge, for instance having a removable cover or face plate, the invention facilitates this by enabling negative-pressure to be used exclusively for the filtration and assay procedures. The cartridge design would not require leak-proof seals or an assembly that withstands internal pressurization since positive pressure does not have to be applied. The removable cover can be a low tolerance press-fit piece that mates with the main cartridge base when vacuum is the basis of operation.

It is to be appreciated that different useful configurations of VCF can be designed of various sizes and volumes and diverse orientations of the ports and vent(s) that still operate within the scope of the invention to employ the application of a vacuum in particular at the vent of an enclosure in order to enable the described usages and advantages. Additionally, different configurations of vacuum-tools to be used with the VCF, as well as the controlled-volume collection apparatus, can likewise be derived yet still be consistent with the aims and functional objectives of the described filtration invention.

Finally to be appreciated, the filtration devices and methods described are not limited in applicability to use with a single VCF, or a VCF containing a single filtration element. Applications can encompass arrangements employing multiple VCF integrated together. Inclusive are renditions of a VCF filtration apparatus containing therein a plurality of discrete fluid-filtering elements, each of which serves or functions separately, and each may be associated with their own individual controlled-volume collection chamber. Such a device has utility for multiple filter-elements to share commonly the filtration of a given fluid.

What is claimed is:

1. A filter apparatus for separating and collecting filterable material from a fluid, the apparatus comprising:
 (i) an enclosed housing capable of holding and passing fluid;
 (ii) a vent through which negative pressure is applied, the vent located in the wall of said enclosed housing;
 (iii) a fluid inlet capable of allowing introduction of fluid into said filter apparatus;
 (iv) a hydrophilic filter confined within said housing capable of allowing filterable material to be separated from said fluid, concentrated and retained within said housing;
 (v) a fluid outlet capable of allowing discharge of fluid out of the filter apparatus; and
 (vi) a hydrophobic filter positioned inside the vent,
  wherein the vent is located on the fluid inlet side of the housing and is capable of actively and continuously delivering negative pressure to the fluid inlet side of the hydrophilic filter;
  wherein the hydrophilic filter separates the fluid inlet from the fluid outlet; and
  wherein the filter apparatus separates and collects filterable material from a fluid.

2. The filter apparatus according to claim 1, wherein said hydrophilic filter includes physical, chemical, biological, charge and/or magnetic based means to separate filterable material from the fluid.

3. The filter apparatus according to claim 1, wherein said hydrophilic filter is a porous filter element capable of removing filterable material from the fluid that is passed through it.

4. The filter apparatus according to claim 3, wherein said porous element is a filter membrane made from materials selected from the group consisting of nitrocellulose, mixed cellulose esters, polyether sulfone, nylon, polycarbonate, polyvinyl, cellulose, glass, ceramics, and alumina.

5. The filter apparatus according to claim 1, wherein said hydrophobic vent may also include a ball-valve, flexible seal or moveable cover.

6. The filter apparatus according to claim 1 having at least one portion thereof made of transmissive material capable of allowing the contents of said filter apparatus to be viewed or measured by optical means.

7. The filter apparatus according to claim 1, wherein said filter apparatus can be opened thereby allowing extraction of separated and retained said filterable material from said filter apparatus.

8. The filter apparatus according to claim 1, wherein said filter apparatus can be opened thereby allowing extraction of said hydrophilic filter from the filter apparatus.

9. The filter apparatus according to claim 1, wherein said filter apparatus is capable of retaining fluid.

10. The filter apparatus according to claim 1, wherein said filter apparatus is capable of being incubated at temperatures up to 70 degrees centigrade.

11. The filter apparatus according to claim 1, wherein said filter apparatus is made of polymeric material selected from the group consisting of polystyrene, polycarbonate, polypropylene, nylon acrylics, silicone and flexible elastomer.

12. The filter apparatus according to claim 1, wherein said negative pressure is applied externally to said vent through a separate suction apparatus comprising:
 (i) means for attaching said suction apparatus to said filtration apparatus;
 (ii) a fluid path capable of delivering continuous and/or intermittent suction to said aspiration means; and (iii) a controller for regulating the timing and amount of suction applied to said aspiration means of said filtration apparatus.

13. The filter apparatus according to claim 12, wherein said fluid path prevents liquid flow from said vent getting into said suction apparatus.

14. The filter apparatus according to claim 12, wherein said suction apparatus further includes:
   a fluid path capable of delivering continuous and/or intermittent suction to said fluid outlet of said filtration apparatus thereby permitting fluid flow through and/or out of said filter apparatus; and
   a controller for regulating the timing, and amount of suction applied to said fluid outlet of said filtration apparatus.

15. The filter apparatus according to claim 14, wherein said aspiration of said fluid into said filter apparatus and the said passage of fluid through said filter apparatus are independently controllable.

16. The filter apparatus according to claim 14, wherein a volume of said fluid exposed to the hydrophilic filter is limited and/or regulated.

17. The filter apparatus according to claim 16, wherein said volume of said fluid is limited and/or regulated using an electronic volumetric meter, mechanical volumetric meter, fixed volume suction apparatus, and/or controlled vacuum pump.

18. The filter apparatus according to claim 14, wherein said volume of said fluid exposed to the hydrophilic filter is limited and/or regulated by a controlled volume collection apparatus utilizing a ball valve, movable flap, and/or hydrophobic vent.

19. The filter apparatus according to claim 1 wherein said filtration apparatus is partitioned to provide a plurality of filters, each separated to function independently.

* * * * *